(12) United States Patent
Hyodo et al.

(10) Patent No.: US 8,056,422 B2
(45) Date of Patent: Nov. 15, 2011

(54) METHOD AND MEMBER FOR MEASURING STRESS DISTRIBUTION OF NATURAL BONE, SYNTHETIC BONE, OR MEMBER ATTACHED TO THEM

(75) Inventors: Koji Hyodo, Ibaraki (JP); Chao-Nan Xu, Saga (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 778 days.

(21) Appl. No.: 11/814,450

(22) PCT Filed: Jan. 11, 2006

(86) PCT No.: PCT/JP2006/300199
§ 371 (c)(1),
(2), (4) Date: Jul. 20, 2007

(87) PCT Pub. No.: WO2006/077756
PCT Pub. Date: Jul. 27, 2006

(65) Prior Publication Data
US 2009/0012431 A1    Jan. 8, 2009

(30) Foreign Application Priority Data

Jan. 21, 2005 (JP) .................................. 2005-014907

(51) Int. Cl.
*G01L 1/24* (2006.01)
(52) U.S. Cl. ........................................................ 73/800
(58) Field of Classification Search .................... 73/800, 73/862.324, 862.624
See application file for complete search history.

(56) References Cited

U.S. PATENT DOCUMENTS
4,265,252 A    5/1981    Chubbuck et al.
(Continued)

FOREIGN PATENT DOCUMENTS
JP    03-012190 A    1/1991
(Continued)

OTHER PUBLICATIONS

International Search Report of PCT/JP2006/300199, date of mailing Apr. 11, 2006.
(Continued)

*Primary Examiner* — Max Noori
(74) *Attorney, Agent, or Firm* — Westerman, Hattori, Daniels & Adrian, LLP (57) ABSTRACT

When visualizing the stress distribution of natural bone, synthetic bone, or a member attached to either thereof without omitted points, in order to measure accurately in a variety of modes using an inexpensive system, a mechanoluminescence material thin film 6 is formed in advance on a bone material peripheral surface 5 in an appropriate area thereof including the portion where an insertion support portion 4 of an artificial hip prosthesis 2 is inserted into a hollow inside 3 of a damaged femur 1 or a synthetic bone simulating the damaged femur. The mechanoluminescence material thin film 6 portion is photographed over its entire circumference with an IICCD camera 7 from the external peripheral side thereof as or after the artificial hip prosthesis 2 is inserted. The obtained image is fed to a computer 11 to obtain a luminescence image 8. The computer 11 outputs the intensities of the received light in the form of an image as is, so that the luminescence image 8 can be obtained easily. Particularly, the data about the intensities of the received light can be used as stress/strain data virtually as is. Such method is also suitable for dynamic analysis.

5 Claims, 8 Drawing Sheets

U.S. PATENT DOCUMENTS

| | | | |
|---|---|---|---|
| 5,018,977 A | | 5/1991 | Wiley et al. |
| 5,247,560 A | * | 9/1993 | Hosokawa et al. ............ 378/54 |
| 5,284,143 A | * | 2/1994 | Rattner ......................... 600/427 |
| 5,695,496 A | * | 12/1997 | Orsak et al. ..................... 606/54 |
| 5,817,945 A | * | 10/1998 | Morris et al. .................. 73/800 |
| 7,060,371 B2 | * | 6/2006 | Akiyama et al. .............. 428/690 |
| 7,080,561 B2 | * | 7/2006 | Bohlmann et al. ............. 73/800 |
| 7,258,817 B2 | * | 8/2007 | Akiyama et al. ........ 252/301.4 R |
| 7,509,872 B2 | * | 3/2009 | Hyodo et al. ................... 73/800 |
| 7,769,550 B2 | * | 8/2010 | Hyodo et al. .................. 702/42 |
| 2001/0017059 A1 | * | 8/2001 | Xu et al. ......................... 73/800 |
| 2003/0181800 A1 | * | 9/2003 | Bonutti ......................... 600/407 |
| 2005/0182325 A1 | * | 8/2005 | Mano et al. ................... 600/437 |
| 2006/0014231 A1 | * | 1/2006 | Van Rompaey et al. ........ 435/21 |
| 2006/0252045 A1 | * | 11/2006 | Chatterjee-Kishore et al. .. 435/6 |

FOREIGN PATENT DOCUMENTS

| | | |
|---|---|---|
| JP | 06-180260 A | 6/1994 |
| JP | 07-311103 A | 11/1995 |
| JP | 2732178 B2 | 3/1998 |
| JP | 2001-215157 A | 8/2001 |
| JP | 2003-518973 A | 6/2003 |
| WO | 01/49173 A1 | 7/2001 |

OTHER PUBLICATIONS

Japanese Office Action dated Oct. 26, 2010, issued in corresponding Japanese Patent Application No. 2006-553862.

Japanese Office Action dated Jun. 22, 2010 issued in corresponding Japanese Application No. 2006-553862.

* cited by examiner

Fig. 1

LUMINESCENCE IMAGE

ICCD CAMERA

COMPUTER

MECHANOLUMINESCENCE MATERIAL THIN-FILM

METHOD AND MEMBER FOR MEASURING STRESS DISTRIBUTION OF NATURAL BONE, SYNTHETIC BONE, OR MEMBER ATTACHED TO THEM

TECHNICAL FIELD

The present invention relates to a method for measuring stress distribution of natural bone, synthetic bone, or a member attached to either thereof, by which the distribution of stress or strain on the bone or the like can be easily measured. The invention also relates to synthetic bone for stress distribution measurement and a member, such as an implant, that is attached to a natural or synthetic bone.

BACKGROUND ART

One of the issues facing the aging society that is gaining increasing attention involves problems concerning the bones, such as the changes in bone density or morphology accompanying the aging of body function, and damages to the bone due to falling accidents or the like. It is particularly important to overcome such problems to achieve "safe, secure, and high-quality life in an aging society."

For example, when an orthopedic implant such as an artificial joint is attached in the event of damage to a bone, the implant attached may cause a dynamic environmental change. This could, under certain conditions, induce a change in the density or morphology of the bone, resulting in the loosening of the implant. Therefore, it is extremely important to monitor the stress distribution in the bone to which the implant is attached as accurately as possible if the attached implant is to maintain appropriate biocompatibility for a desired period of, for example, 20 years or longer.

For the analysis of bone stress distribution, conventionally the strain gauge method has been used whereby, particularly for the measurement of surface stress distribution, a number of strain gauges are affixed to the surface of a bone so as to analyze stress distribution based on the stress applied to the bone and the output signals from the individual strain gauges. However, the number of such affixed strain gauges is limited and it has been impossible to conduct measurement without omitted points.

As a countermeasure, the thermoelastic stress measurement method has recently been developed by which surface stress is visualized on the basis of the surface temperature of a sample, which varies depending on stress. This technique, based as it is on infrared thermography, makes it possible to visualize the surface stress distribution in a femur, for example, to which an artificial joint is attached, without omitted points.

Meanwhile, the applicants have conducted studies on inorganic materials that emit light in response to application of mechanical energy, and have successfully manufactured a material from inorganic substances consisting of a base material that is a piezoelectric body with wurtzite type structure, in particular, and a luminescence center, as disclosed in Patent Document 1. The applicants have found that when a luminescence center is added to the base material, the light-emission intensity of an obtained thin film can be significantly increased. The applicants have filed a patent application for this discovery. Subsequent studies have led to the discovery of a variety of inorganic materials that emit light based on the force, and studies are also underway to utilize such materials in various fields. This is disclosed, for example, in Patent Document 2, in which detection of abnormal stress prior to the destruction of concrete by mixing a mechanoluminescence material in the concrete is proposed.

Patent Document 1: JP Patent Publication (Kokai) No. 11-120801 A (1999) (U.S. Pat. No. 3,265,356)
Patent Document 2: JP Patent Publication (Kokai) No. 2003-137622 A

DISCLOSURE OF THE INVENTION

Problems to be Solved by the Invention

As described above, the thermoelastic stress measurement method is capable of solving the problem of omitted-measurement points during the analysis of bone stress/strain distribution by the strain gauge method, enabling the visualization of the bone surface stress distribution without omitted points. However, in order to detect the heat that varies depending on stress by this technique, minute temperature changes on the order of several mK must be captured by infrared thermography. Another problem is that, in order to obtain practical temperature (stress) distribution accuracy, thermography with higher temperature resolution must be used, and in addition an image processing system for image integration or the like is required, which is inevitably expensive. Furthermore, the aforementioned technique in principle measures the sum of principal stresses and cannot measure shear stress.

Thus, it is the main object of the invention to provide a technique to measure the stress distribution of natural bone, synthetic bone, or a member attached to either thereof in a visual manner without omitted points accurately and in various modes, using an inexpensive system.

Means of Solving the Problems

In order to solve the aforementioned problems, the invention utilizes the materials previously developed by the applicant that emit light in response to mechanical energy. More specifically, the invention provides a method for measuring the stress distribution of natural bone, synthetic bone, or a member attached to either thereof. The method comprises: providing a mechanoluminescence material layer on the surface of natural bone, synthetic bone, or member attached to either thereof, and measuring light emitted by the mechanoluminescence material upon application of stress to the bone with a camera.

Another method of measuring the stress distribution of synthetic bone according to the invention comprises: mixing a mechanoluminescence material in the material of the synthetic bone, and measuring light emitted by the mechanoluminescence material due to stress applied to the bone with a camera to measure the stress distribution on the surface of or inside the synthetic bone.

Another method of measuring the stress distribution of synthetic bone comprises: providing a mechanoluminescence material layer inside the synthetic bone, and measuring light emitted by the mechanoluminescence material due to stress applied to the bone with a camera to measure the stress distribution on the surface of or inside the synthetic bone.

Another method of measuring the stress distribution of synthetic bone according to the invention comprises: providing a mechanoluminescence material layer on an internal surface of a synthetic bone formed of transparent material, and measuring light emitted by the mechanoluminescence material due to stress applied to the bone with a camera from the outside of the bone material, so as to measure the stress distribution on the internal surface of the synthetic bone.

Another method of measuring the stress distribution of synthetic bone comprises: providing a mechanoluminescence material layer between a number of layers of transparent material of which the synthetic bone is formed, and measuring light emitted by the mechanoluminescence material due to stress applied to the bone with a camera, to measure the stress distribution inside the synthetic bone.

A synthetic bone according to the invention comprises a mechanoluminescence material layer on the surface thereof.

Another synthetic bone according to the invention is made of the material mixed with a mechanoluminescence material.

Another synthetic bone according to the invention comprises a number of layers of transparent material between which a mechanoluminescence material layer is provided.

Another synthetic bone according to the invention comprises a mechanoluminescence material layer on the surface thereof and is formed in the shape of a stress-measurement test piece.

A member for measuring stress according to the invention comprises a mechanoluminescence material layer on the surface of the member and is attached on a natural bone or synthetic bone.

Effects of the Invention

The aforementioned structures of the invention allow the stress distribution of bone to be measured without omitted points in a visual manner accurately and in a variety of modes, using an inexpensive system.

EXPLANATION OF THE REFERENCE NUMERALS

1 damaged femur
2 artificial hip joint
3 canal
4 insertion support portion
5 external bone surface
6 mechanoluminescence material thin-film
7 ICCD camera
8 luminescence image
9 external surface
10 internal bone surface
11 computer
12 load means

BEST MODE OF CARRYING OUT THE INVENTION

The present invention, when measuring the distribution of stress or strain (to be hereafter simply referred to as stress) of bone, employs the aforementioned inorganic materials that emit light based on mechanical energy, instead of the conventional method using infrared thermography. While such inorganic materials are disclosed in the aforementioned Patent Document 1, for example, they are described briefly in the following.

The mechanoluminescence material employed by the present invention comprises an inorganic base material in which a luminescence center is doped, the dope consisting of one or more of rare earths and transition metals that emit light as the electrons excited by mechanical energy return to ground state. Examples of the inorganic base material are oxides sulfides, carbides, and nitrides of melilite structure, $FeS_2$ structure, wurtzite structure, spinel structure, corundum structure, or β-alumina structure. Of these, oxides having melilite structure, $FeS_2$ structure, wurtzite structure, spinel structure, corundum structure, or β-alumina structure are preferable. Examples having melilite structure include $CaYAl_3O_7$, $Ca_2Al_2SiO_7$, $Ca_2(Mg,Fe)Si_2O_7$, $Ca_2B_2SiO_7$, $CaNaAlSi_2O_7$, $Ca_2MgSi_2O_7$, $(Ca,Na)_2(Al,Mg)(Si,Al)_2O_7$, and $Ca_2(Mg,Al)(Al,Si)SiO_7$. Examples having $FeS_2$ structure include materials having $Sr_3Al_2O_6$, $Ca_3Al_2O_6$, $CaC_2$, $CoS_2$, $MnS_2$, $NiS_2$, $RuS_2$, and $NiSe_2$ as a principal component. Examples having wurtzite structure include materials having BeO, ZnO, ZnS, CdS, MnS, AlN, GaN, InN, TaN, NbN, and α-SiC as a principal component. Examples having spinel structure include $MgAl_2O_4$ and $CaAl_2O_4$. An example having corundum structure is $Al_2O_3$. An example having β-alumina structure is $SrMgAl_{10}O_{17}$.

Preferably, the luminescence center with which these inorganic base materials are doped consists of one or more of rare earth ions Sc, Y, La, Ce, Pr, Nd, Pm, Sm, Eu, Gd, Tb, Dy, Ho, Er, Tm, Yb, and Lu, and transition metal ions Ti, Zr, V, Cr, Mn, Fe, Co, Ni, Cu, Zn, Nb, Mo, Ta, and W. Of these, in a case where the inorganic base material is gehlenite, for example, a rare earth metal, particularly Ce ion, is preferable. The amount of doping of the luminescence center is preferably from 0.001 to 20 weight %, particularly from 0.001 to 5 weight %, in the mechanoluminescence material, from the viewpoint of light-emission intensity and emission efficiency.

Figure 1:
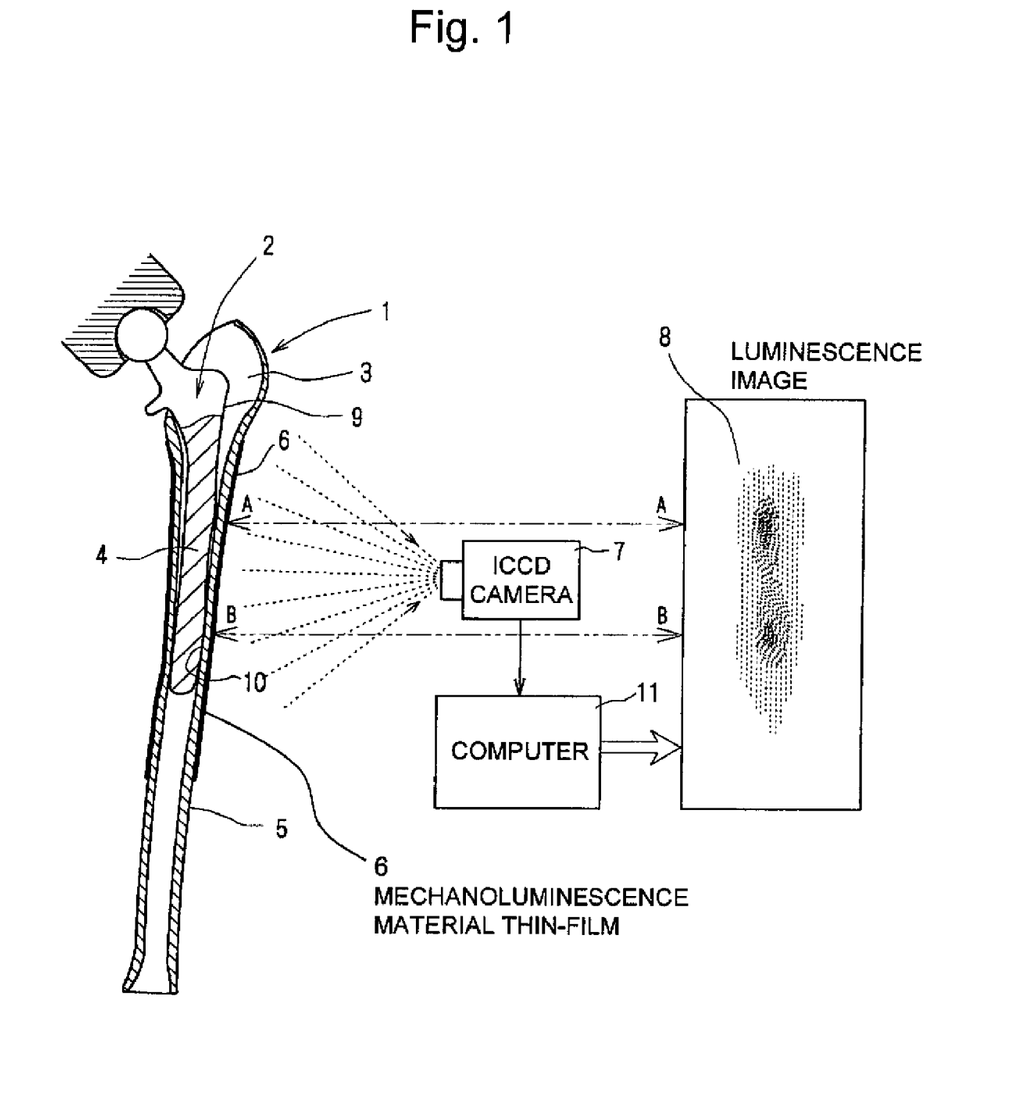
FIG. 1 shows a system configuration of an embodiment of the invention.

In accordance with the invention, the mechanoluminescence materials can be used to measure whether or not, when implanting an artificial hip prosthesis 2 in a damaged femur 1, for example, as shown in FIG. 1, the artificial hip prosthesis is inserted within the inner walls of a hollow inside 3 of the damaged femur 1 comfortably. More specifically, in the illustrated example, an insertion support portion 4 of the artificial hip prosthesis 2 is inserted in the hollow inside 3 of the damaged femur or a synthetic damaged femur (to be hereafter generally referred to as damaged femur), which is prepared by copying the form of the damaged femur as an experimental sample. A mechanoluminescence material thin film 6 is provided on a bone-material external peripheral surface 5 of the damaged femur 1 in an appropriate area thereof as a mechanoluminescence material layer, by coating the surface with a mechanoluminescence material, or by any other method, the area including the portion where the insertion support portion 4 is inserted.

Figure 2:
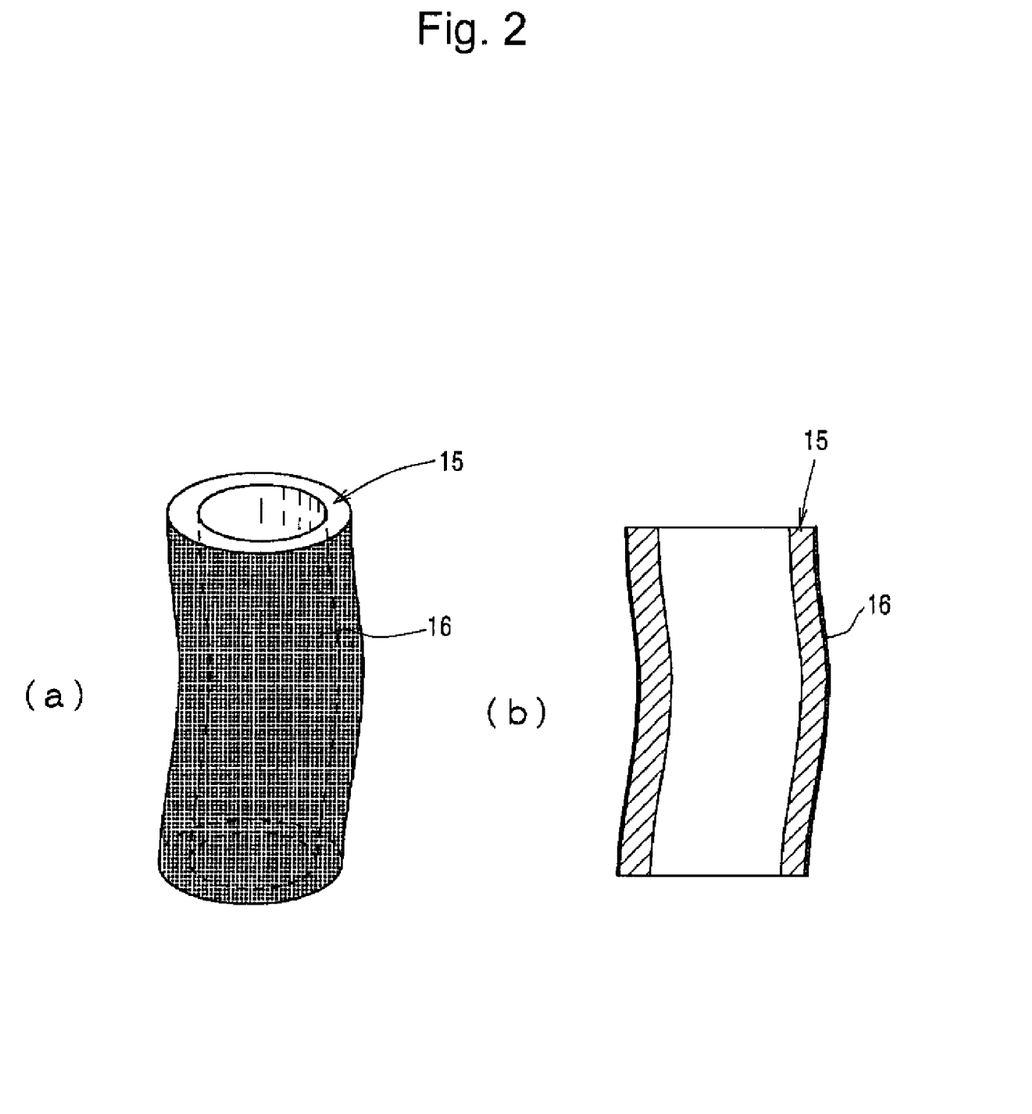
FIG. 2 shows an example of application of the invention.

FIG. 2 schematically shows such mechanoluminescence material layer as formed. On the entire or partial surface of the bone material peripheral surface of a test material 15 corresponding to the damaged femur 1, a mechanoluminescence thin film 16 consisting of a mechanoluminescence material is formed. There are various methods available for forming such thin film of mechanoluminescence material. For example, the adherence strength of the mechanoluminescence material thin film 6 can be significantly increased by vacuum seal treatment or vacuum heat treatment.

A main part or the entire circumference of the mechanoluminescence material thin film 6 is photographed from the external peripheral side with an ICCD camera 7 as and after the artificial hip prosthesis 2 is inserted, as shown in FIG. 1, while a predetermined load is applied by a load means 12. The thus photographed image is fed to a computer 11 to obtain a luminescence image 8. The camera used for photography may be any of a variety of other conventional cameras, such as a CCD camera, other than the ICCD camera. In the computer 11, image processing, such as integration that is performed conventionally when measuring the distribution of heat caused by stress and displaying it in an image, is not necessarily required; the luminescence image 8 can be easily obtained by outputting the intensities of received light as is in the form of an image. Particularly, the data about received light intensities can be utilized as stress/strain data virtually as is. The technique is thus also suitable for dynamic analysis.

In the luminescence image 8 shown in FIG. 1, the external peripheral surface 9 of the insertion support portion 4 of the artificial hip prosthesis 2 strongly abuts on the internal peripheral surface 10 of the hollow inside 3 of the damaged femur 1 at portions A and B. These portions A and B are shown in the luminescence image 8 as strong light-emission intensity portions, about which the state of stress distribution can be detected as a light-emission intensity distribution. By measuring the light-emission intensity, the stress distribution on the surface of the damaged femur 1 can be measured with reference to load condition/light-emission intensity correlation data that is known in advance.

Figure 3:
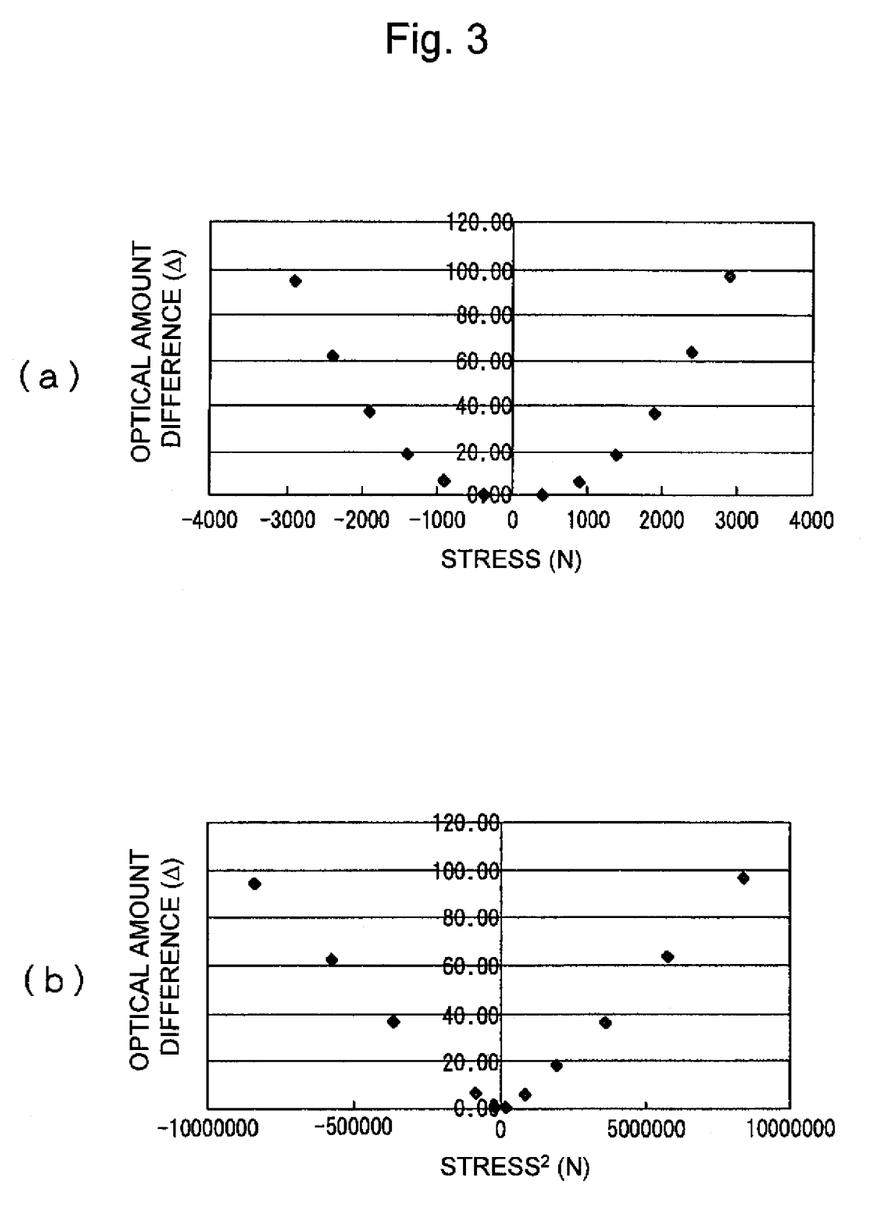
FIG. 3 shows another example of application of the invention.

FIG. 3 shows the results of differential luminance measurement with PhotoshopCS based on emission detection using Hamamatsu C2400-30 (IICCD analog 8-bit), using a test piece of synthetic bone material consisting of glass-filled epoxy resin having a JIS-complying shape measuring 25 mm in width and 5.5 mm in thickness, where the inter-chuck distance was 87 mm and the rate of loading was 6 kN/sec on MTS Minibionix 858. FIG. 3(a) shows the (load)–(optical amount difference) characteristics; FIG. 3(b) shows the characteristics in terms of (load)$^2$–(optical amount difference). As is seen from FIG. 3(b) in particular, linear characteristics are obtained, allowing an accurate stress/strain condition determination from the light amount data. The above characteristics are reversible, so that a highly practical stress distribution measurement method can be realized by, for example, applying a plurality of artificial hip prostheses 2 having various shapes to the damaged femur coated with the mechanoluminescence material as test piece and selecting a most appropriate one.

Figure 4:
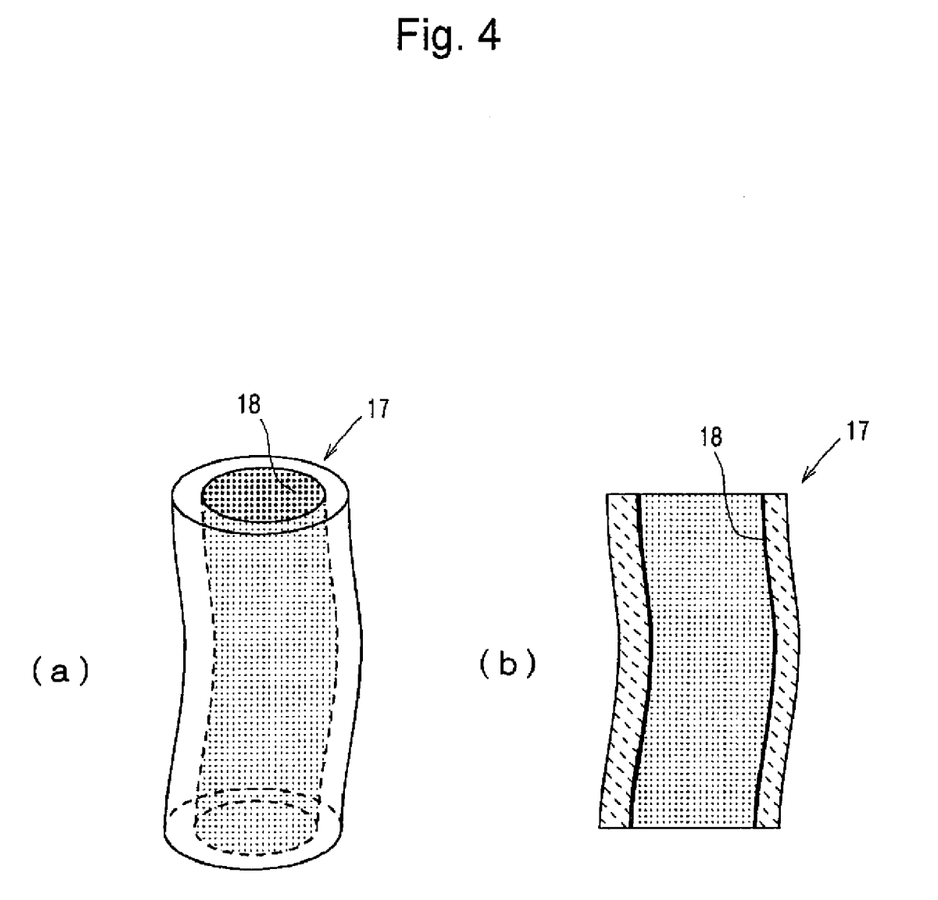
FIG. 4 shows yet another example of application of the invention.

In the above-described stress distribution measurement method, in addition to the mechanoluminescence thin film 16 formed on the external surface of the test material 15 as shown in FIG. 2, a test material 17 may be formed as a synthetic bone as shown in FIG. 4 from a transparent material such as synthetic resin, and then a mechanoluminescence thin film 18 may be formed on the internal peripheral surface of the bone material. By observing the test material 17 from the external periphery side thereof using an ICCD camera or the like in the same way as described above as the insertion support portion of the above-described artificial hip prosthesis is inserted, it becomes possible to detect the stress distribution state on the internal peripheral surface, such as how a large force is acting on a particular location, for example. In this embodiment, when measuring the stress distribution on the internal peripheral surface of the bone material, the synthetic bone is made of a transparent material so as to allow measurement via the external peripheral surface of the bone material. However, even in cases of natural bone or nontransparent synthetic bone, it is also possible to conduct the measurement with the mechanoluminescence thin film 18 formed on the internal peripheral surface of the bone material if an endoscope or a small-sized camera is used.

Figure 5:
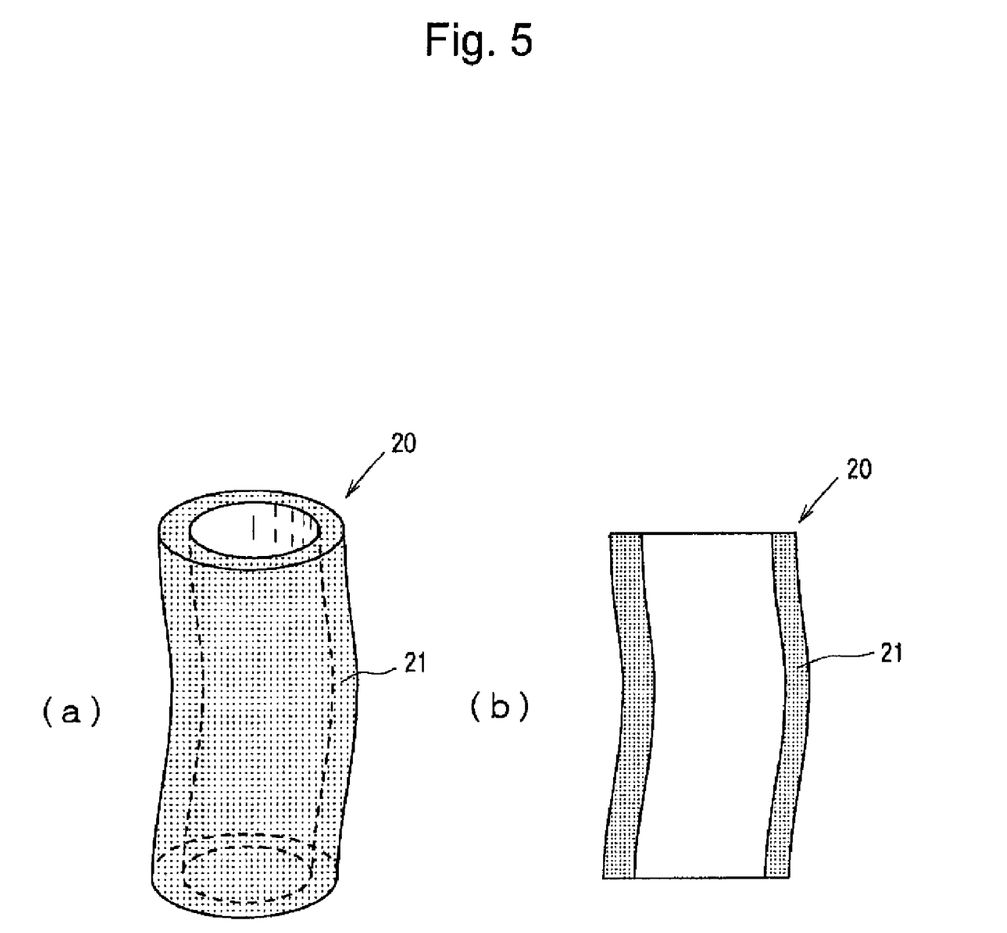
FIG. 5 shows yet another example of application of the invention.

Furthermore, a test material with a predetermined shape may be formed by mixing mechanoluminescence material powder 21 in the bone material when preparing a test material 20 for a synthetic bone, as shown in FIG. 5. When the test material 20 in which such mechanoluminescence material is mixed is observed via its external periphery with the ICCD camera or the like after an artificial hip prosthesis similar to the one described above is inserted, the mechanoluminescence material exposed on the peripheral surface, particularly, of the test material 20 emits light depending on stress, thereby allowing the measurement of the stress distribution condition on the surface of the test material 20. Alternatively, the test material 20 may consist of a transparent material such as synthetic resin, and the above-described mechanoluminescence material powder 21 may be mixed in the resin. In this case, the state of light emission inside the material can also be observed, and, by identifying the location of such emission, it becomes possible to know what stress distribution is present at which portion of the material.

Figure 6:
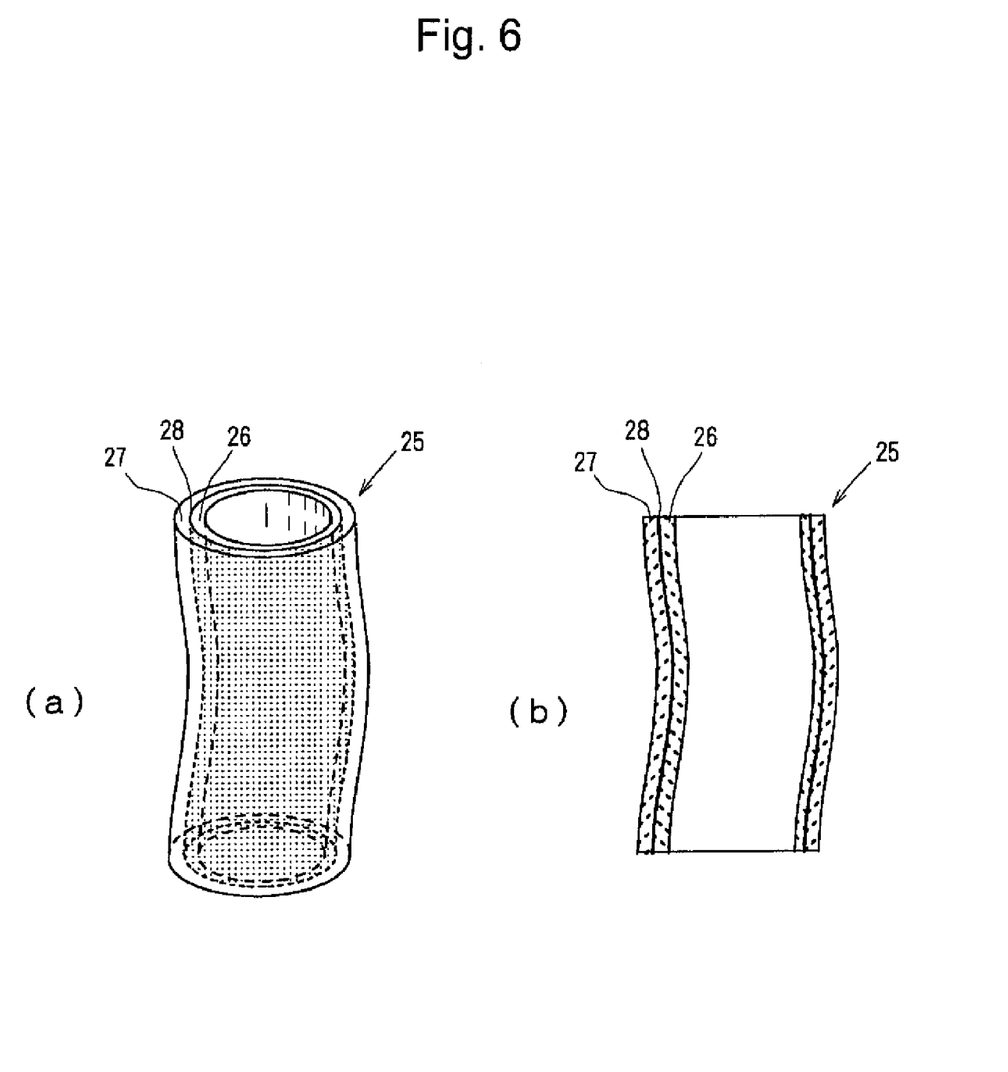
FIG. 6 shows yet another example of application of the invention.

Further alternatively, a test material 25 as a synthetic bone may be comprised of two layers, namely: an inner transparent material 26 and an outer transparent material 27, between which a mechanoluminescence material layer 28 is disposed, as shown in FIG. 6, for example. Such test material can be manufactured by coating the external peripheral surface of the inner transparent material 26 having a predetermined shape with the mechanoluminescence material layer, and then further forming the outer transparent material 27 having a predetermined shape on the outside of the mechanoluminescence material layer. After the insertion of the artificial hip joint into the test material 25 with an ICCD camera or the like in the same manner as described above, the internal stress distribution can be known.

Figure 7:
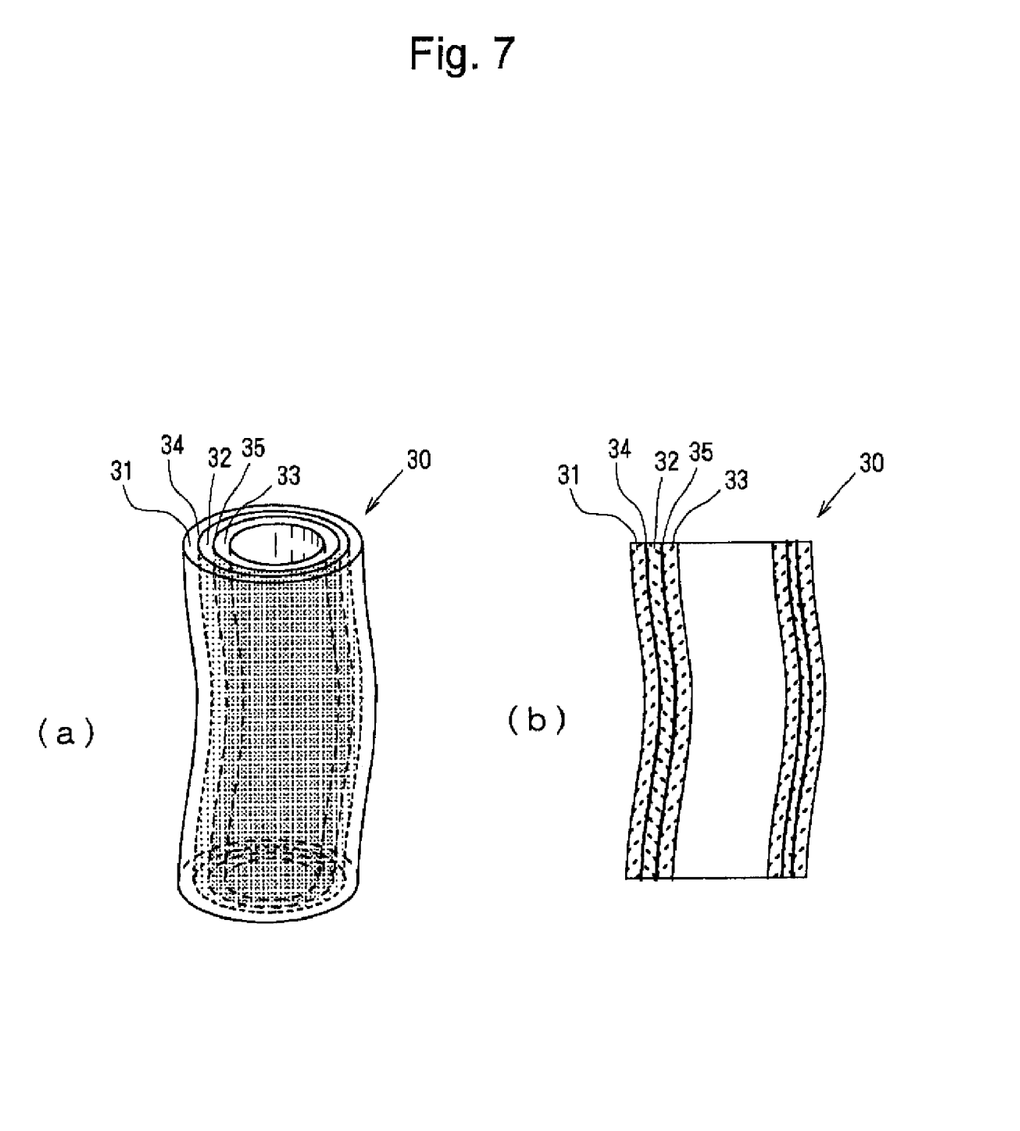
FIG. 7 shows yet another example of application of the invention.

Further, as shown in FIG. 7, for example, a test material 30 may be formed of an outer transparent material 31, an intermediate transparent material 32, and an inner transparent material 33. By providing an outer mechanoluminescence material layer 34 between the outer transparent material 31 and the intermediate transparent material 32, and an inner mechanoluminescence material layer 35 between the intermediate transparent material 32 and the inner transparent material 33, it becomes possible to observe the stress distribution state as regards the two internal layers, as opposed to the example of FIG. 6 where only one internal layer is observable. Even greater numbers of layers may be formed in the test material using this method, to allow more detailed observation of the inside of the test material.

In the foregoing examples, layers were formed from the inside to the outside when providing the mechanoluminescence material layer within a synthetic bone made of a transparent material. Alternatively, for example, the mechanoluminescence material layer may be formed on a surface that appears when a transparent test material is divided in a direction parallel to the axis of the test material, and then the divided pieces may be integrated again. Such test material also allows the measurement of the stress distribution in a plane from the inside to the outside by the same technique.

Figure 8:
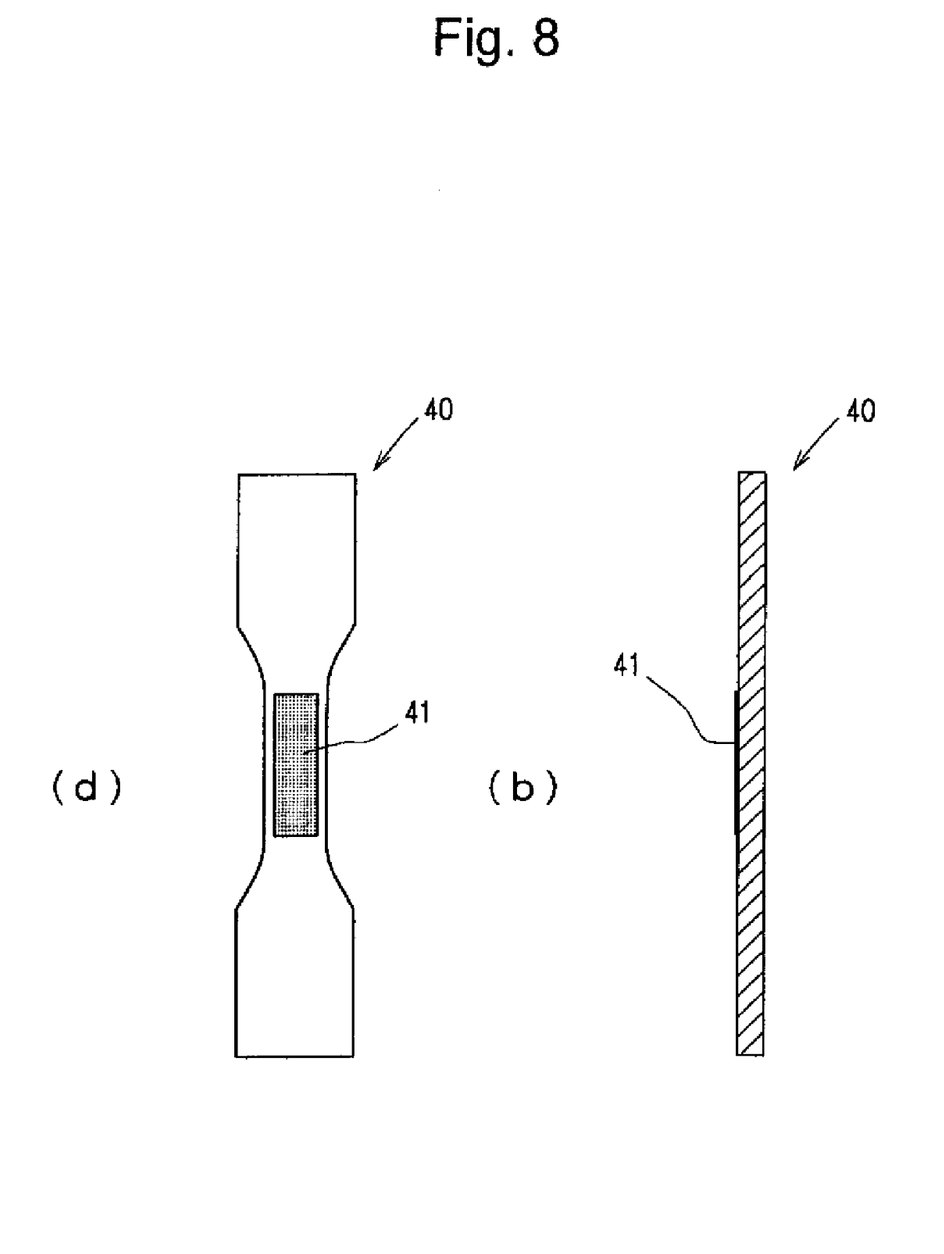
FIG. 8 shows yet another example of application of the invention.

While the foregoing embodiments invariably involved inserting an artificial hip prosthesis into a damaged femur, that was for the sake of explanation; the invention can be applied for the measurement of stress distribution in a variety of other kinds of natural bone and synthetic bone. For example, besides the synthetic bone in the embodiments that simulates the shape of an actual bone, a test piece shaped as shown in FIG. 8 may be used. By providing a mechanoluminescence material thin film 41 on the surface of a synthetic bone 40 having such test piece shape and observing the synthetic bone 40 on stress test equipment with an ICCD camera or the like, it can be seen what stress distribution the material of the synthetic bone has.

While the foregoing embodiments showed examples where the mechanoluminescence material layer was provided on the surface of natural bone or synthetic bone, it is also possible to provide the mechanoluminescence material layer on the surface of the artificial hip prosthesis 2, such as shown in FIG. 1, by coating or otherwise and then observe the surface stress distribution on the artificial hip prosthesis 2 when it is inserted in a transparent synthetic bone, externally of the synthetic bone. In this way, the mechanoluminescence material allows observation of relative stress conditions between the bone material and any of a variety of objects that is applied to the bone material; it should be obvious, therefore, that the mechanoluminescence material layer may be disposed on either side.

Furthermore, this technique can be applied for the measurement of the application state of a biological hard tissue and an associated material in the same way as in the foregoing embodiments, such as for the measurement of relative stress distribution states between the jaw bone and an artificial tooth mounted thereon. Therefore, the term "natural bone or synthetic bone" in the invention may encompass such biological hard tissue as a whole.

The above-described stress measurement technique can be used not just for the measurement of the mechanical state of a biological hard tissue and a member attached to the hard tissue; the technique can also be used for medical education purposes, for example, to determine whether or not an object such as an artificial hip prosthesis has been appropriately attached to a synthetic bone, or whether or not the level of attaching skill has improved, based on the observation and comparison of differences in stress distributions when the object was attached appropriately by a skilled worker and when the same object was attached by a trainee.

In another example, in a case where an actual implanted bone has been used appropriately for a long period of e.g. 10 years, the stress distribution of the implanted bone can be measured by the technique of the invention upon detaching it; later, the measured stress distribution can be compared with the state of stress distribution measured upon attaching another, new implant. In this way, it can be known whether or not such new implant could be appropriately attached. Thus, the invention can be used for a variety of purposes. While the foregoing description of embodiments was made with regard to stress distribution, it goes without saying that similar measurement can be made concerning strain caused in association with stress.

INDUSTRIAL APPLICABILITY

As described above, the invention can be used in a variety of modes for the purpose of measuring the state of application of a biological hard tissue and a substance associated with the biological hard tissue, such as the stress distribution in a natural bone per se, the stress distribution in a synthetic bone simulating the natural bone, the stress distribution characteristics of synthetic bone materials for various synthetic bones, and the observation of the state of attachment of an artificial tooth, for example. Furthermore, based on a comparison with an appropriate example as mentioned above, the invention can be used for educational purposes or for selecting an appropriate implant. In the present invention, identification of the light emission site may be facilitated by additionally using a light-blocking substance or layer.

The invention claimed is:

1. A synthetic bone comprising:
   a mechanoluminescence material and
   a number of layers of transparent material between which a mechanoluminescence material layer is provided for said synthetic bone.

2. The synthetic bone according to claim 1, comprising a mechanoluminescence material layer on the surface of the bone.

3. The synthetic bone according to claim 1, which is made of the material comprising a mechanoluminescence material.

4. The synthetic bone according to claim 1, comprising a mechanoluminescence material layer on the surface thereof and is formed in the shape of a stress measurement test piece.

5. The synthetic bone according to claim 1, further comprising a light-blocking substance or layer.

* * * * *